United States Patent [19]
Gilbert

[11] Patent Number: 5,125,274
[45] Date of Patent: Jun. 30, 1992

[54] TUBE TESTING APPARATUS

[75] Inventor: Dennis H. Gilbert, Kennewick, Wash.

[73] Assignee: Sandvik Special Metals Corporation, Kennewick, Wash.

[21] Appl. No.: 609,775

[22] Filed: Nov. 7, 1990

[51] Int. Cl.⁵ .................... G01N 29/24; G01N 29/10
[52] U.S. Cl. ........................... 73/622; 73/623; 73/640
[58] Field of Search ............ 73/622, 623, 628, 629, 73/627, 637, 638, 639, 640, 642

[56] References Cited

U.S. PATENT DOCUMENTS

| | | | |
|---|---|---|---|
| 3,107,521 | 1/1961 | McClure | 73/640 |
| 3,121,324 | 2/1964 | Cowan | 73/67.5 |
| 4,089,227 | 5/1978 | Falgari et al. | 73/622 |
| 4,361,044 | 11/1982 | Kupperman et al. | 73/623 |
| 4,562,738 | 1/1986 | Nakayama et al. | 73/622 |
| 4,580,451 | 4/1986 | Miwa et al. | 73/626 |

FOREIGN PATENT DOCUMENTS 316005  11/1971  U.S.S.R. ........................ 73/622

Primary Examiner—Hezron E. Williams
Assistant Examiner—Rose M. Finley
Attorney, Agent, or Firm—Burns, Doane, Swecker & Mathis

[57] ABSTRACT

A test apparatus for testing objects such as tubing is disclosed. The apparatus includes a rotatively fixed transducer and a rotating lens, wherein the transducer receives an input signal and converts it into an emitted wave energy, the lens focuses the emitted wave energy onto the tubing and focuses reflected wave energy from the tubing back onto the transducer, and the transducer receives the reflected wave energy and converts it into an output signal. The transducer can be provided on one support shell and the lens can be provided on another support shell. One of the support shells can then be positioned within the other support shell. The apparatus is useful for performing dimensional tests and longitudinal and circumferential flaw tests on tubing.

28 Claims, 2 Drawing Sheets

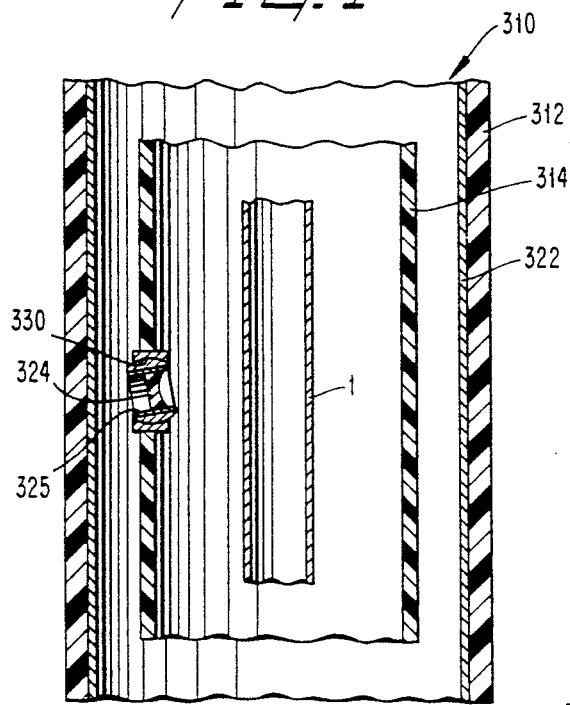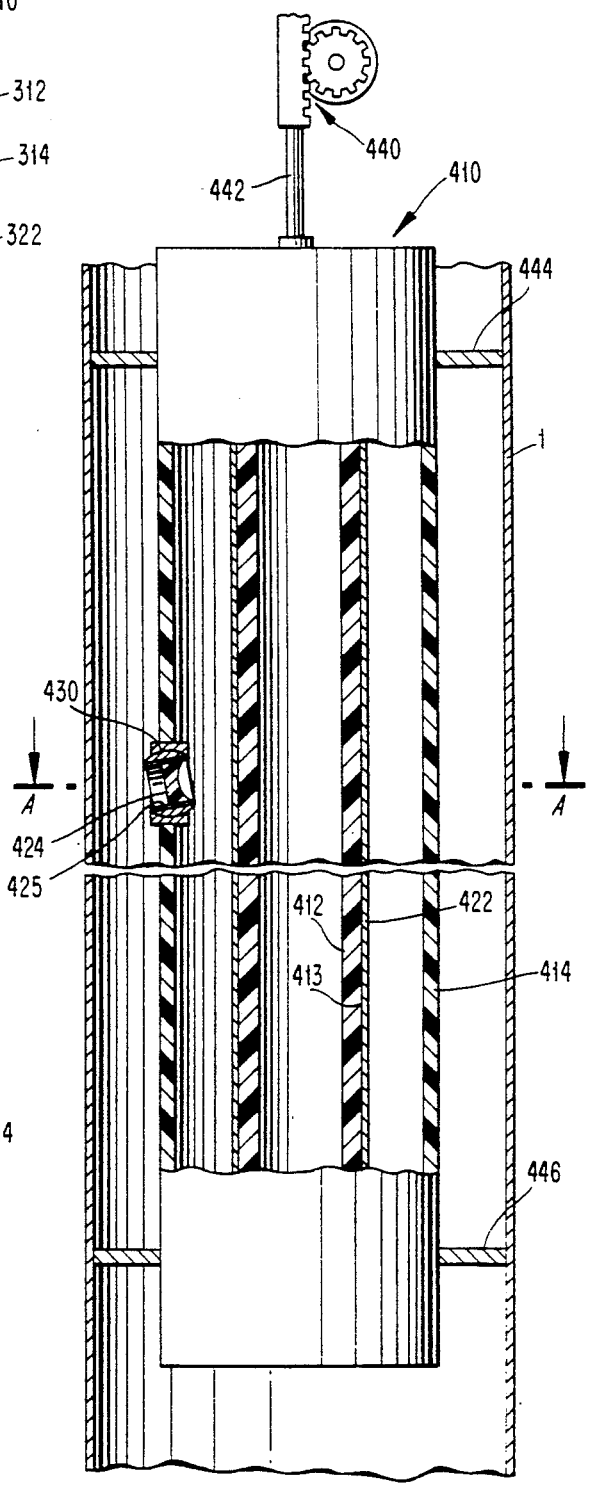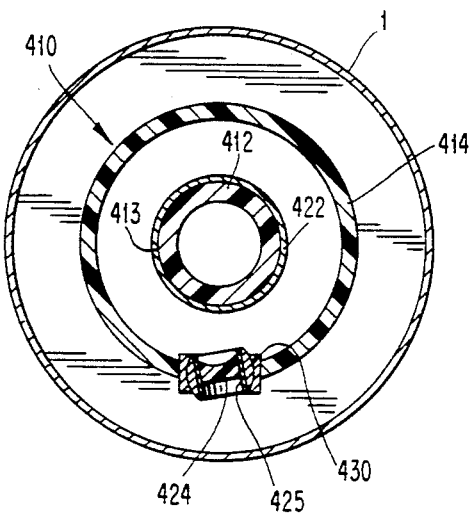

TUBE TESTING APPARATUS

BACKGROUND OF THE INVENTION

1. Field of the Invention

The present invention relates to apparatuses useful for testing objects using wave energy. More particularly, the present invention relates apparatuses useful for testing tubing using ultrasonic wave energy.

2. Description of the Prior Art

Several types of devices are known in the prior art which are adapted to test tubing using wave energy. Conventional ultrasonic testing of tubing involves a high speed rotation of the tubing, i.e., rotation at approximately 2500 rpm. The disadvantage of an apparatus employing such a method is that a mechanical drive system of such an apparatus is normally plagued both by slippage of the tubing, which drastically reduces the accuracy of the testing, and by low throughput of the tubing through the apparatus, which increases the cost and decreases the efficiency of the testing.

Other testing apparatuses are known which do not involve rotation of a test object, but which do involve the rotation of a set of transducers. For example, U.S. Pat. No. 4,562,738 granted to Nagayama et al. discloses an automatic flaw detection device which includes a supporting frame, a rotational frame which rotates freely inside the supporting frame, and ultrasonic searching units which are mounted on the rotating frame and which probe a material passing through the device, wherein signals are sent to and from the searching units through a rotor section and a stator section. Similarly, a system is known in which multiple transducers are mounted on a large head which rotates at several thousand rpm to test a tube that is not rotating.

The disadvantage of such apparatuses is that the need to electrically connect the rotating transducers to a stationary sensor or memory greatly complicates the design of such apparatuses, as is evident in the Nakayama et al. device, which includes a rotor section and a stator section for rotational-to-stationary electrical connection. The complicated designs of these apparatuses necessarily make them more expensive and more prone to break down.

Still other types of devices which involve non-rotating test objects and stationary transducers are known for testing tubing using wave energy. U.S. Pat. No. 3,121,324 granted to Cowan discloses an ultrasonic inspection apparatus for inspecting cylindrical bars, which includes two stationary transducers and a rotating reflector which directs pulsed ultrasound from one of the transducers through a cylindrical bar onto the other of the transducers. U.S. Pat. No. 4,089,227 granted to Falgari et al. discloses an ultrasonic apparatus for measuring the radial dimensions of a cylindrical tube, which includes two stationary transducers which emit pulsed ultrasound, a rotating disk having two openings through which the pulses pass, and a cone-shaped mirror which reflects the pulses onto the tube and which reflects echoes from the tube back to the transducers through the openings. U.S. Pat. No. 4,361,044 granted to Kupperman et al. discloses a scanning ultrasonic probe assembly which fits inside a tube to make various geometric measurements of the tube, wherein the assembly includes two non-rotating transducer assemblies, and two rotating mirrors which reflect ultrasonic signals from the transducer assemblies onto the tube, and from the tube back to the transducer assemblies.

These types of apparatuses have the disadvantage, however, that they are able to perform only a single type of test on a test object, and/or that they are still fairly complicated in design.

U.S. Pat. No. 4,580,451 granted to Miwa et al. discloses an ultrasonic sector-scan probe for observing living tissue, which includes a linear array of ultrasonic transducer segments arrayed on a circular arc, and a window which includes a converging lens or a diverging lens to focus on ultrasound beam from the liner array onto the living tissue. However, the probe of the Miwa et al. patent is only usable for one stationary sector scan at a time, and thus is limited in usefulness for applications where large portions or lengths of tubing need to be tested rapidly.

OBJECTS AND SUMMARY OF THE INVENTION

It is an object of the present invention to avoid or alleviate the problems of the prior art.

It is another object of the present invention to provide an improved apparatus which is readily capable of testing tubing using wave energy.

A further object of the present invention is to provide an apparatus for testing tubing which permits tubing to be throughput at a relatively high rate of speed with relatively minimal slippage of the tubing.

It is a further object of the present invention to provide an apparatus for testing tubing which is relatively simple, inexpensive to construct, which breaks down relatively rarely and which wears out relatively infrequently.

It is a further object of the present invention to provide an apparatus for testing tubing which is capable of testing a variety of different-sized lengths of tubing with only minimal adjustment.

It is a further object of the present invention to provide an apparatus for testing tubing which is capable of performing a plurality of tests on the tubing.

It is a further object of the present invention to provide an apparatus for testing tubing which is capable of rapidly testing large portions or lengths of the tubing.

In one aspect of the present invention, there is provided a test apparatus for testing tubing using wave energy, comprising: a rotatively fixed transducer; and a rotating lens, said transducer receiving an input signal and converting said input signal into an emitted wave energy, said lens focusing said emitted wave energy onto the tubing and focusing reflected wave energy from the tubing back onto said transducer, and said transducer receiving said reflected wave energy and converting said reflected wave energy into an output signal.

In another aspect of the present invention, there is provided a test apparatus for testing tubing using wave energy, comprising: converting means for converting an input signal into an emitted wave energy, and for converting a reflected wave energy reflected by the tubing into an output signal; and rotating focusing means for focusing said emitted wave energy from said converting means onto the tubing, and for focusing said reflected wave energy from the tubing onto said converting means.

In another aspect of the present invention, there is provided an ultrasonic tubing test apparatus for testing tubing using ultrasound, comprising: a first cylindrical, rotatively fixed support shell; a second cylindrical, rotatable support shell located inside said first support shell and disposed around the tubing; a transducer mounted on an inner wall of said first support shell; and a lens mounted in a wall of said second support shell such that an electrical input signal inputted to said transducer which is converted by said transducer to ultrasonic wave energy is focused onto the tubing by the lens, and such that ultrasonic wave energy reflected by the tubing is focused by said lens onto said transducer whereby it is converted into an electrical output signal.

In yet another aspect of the present invention, there is provided an apparatus for focusing emitted wave energy from an emitter onto a length of tubing and for focusing reflected wave energy from the tubing onto a sensor, comprising: a rotatable support shell extending around the tubing, said support shell being made of a material which is absorptive of said emitted and reflected wave energies; a lens mounted in a wall of said support shell, said lens being made of a material which is transmissive of said emitted and reflected wave energies; and means for rotating said support shell about the tubing, said lens for focusing said emitted wave energy onto the tubing and focusing said reflected wave energy onto the sensor as said support shell rotates.

BRIEF DESCRIPTION OF THE DRAWINGS

The preferred embodiments of the present invention will be described in greater detail with reference to the accompanying drawings, wherein like members bear like reference numerals and wherein:

FIG. 4 is a longitudinal cross-sectional view of a fourth embodiment of the test apparatus of the present invention;

FIG. 5 is a partial cutaway side view of a fifth embodiment of the test apparatus of the present invention; and FIG. 6 is a cross-sectional view taken along line A—A of FIG. 5.

DETAILED DESCRIPTION OF THE PREFERRED EMBODIMENTS

Figure 1:
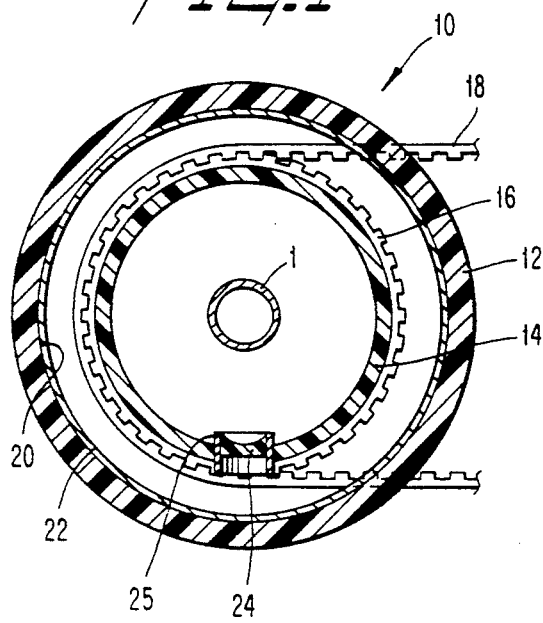
FIG. 1 is a cross-sectional view of a first embodiment of the test apparatus of the present invention.

With reference to FIG. 1, a first embodiment of the test apparatus embodying the general principles of the present invention will be described hereinbelow. A test apparatus 10 in accordance with the first embodiment of the present invention includes a first fixed cylindrical support shell 12, and a second rotatable cylindrical support shell 14. The first support shell 12 extends circumferentially around the second support shell 14, and both support shells 12,14 extend circumferentially around a test object such as a length of tubing 1. A circumferential toothed ring 16 is rigidly fixed to one end of the second support shell 14. The toothed ring 16 mates engagingly with a toothed belt 18 which extends around a portion of the circumference of the second support shell 14, and the toothed belt 18 is drivingly connected to a motor (not shown) so that the second support shell 14 can be rotated.

A cylindrical, sheet-like transducer 22 is mounted in a fixed position on an inner wall 20 of the first support shell 12 such that it is held stationary with the first support shell 12. Also, a lens 24 is mounted in a lens support tube 25 which is mounted in the wall of the second support shell 14 such that it is rotatable with the second support shell 14. The lens 24 may be mounted in a fixed position in the support tube 25, or more preferably it may be mounted such that it is movable in the radial direction of the second support shell 14 to allow its focal point to be moved to a point on the outer diameter of the tubing 1.

The transducer 22 has connected thereto a plurality of electrical connections (not shown) which carry electrical input signals to the transducer 22, and which carry electrical output signals from the transducer 22. The transducer 22 is preferably of the type that produces ultrasonic wave energy when electrical current runs therethrough, and which produces electrical current therein when exposed to ultrasonic wave energy. A preferred material from which the transducer 22 may be made is poled polyvinylidene fluoride (PVDF), although any other suitable material may be used. The lens 24 can be made from any material which is transmissive of ultrasound, although polystyrene or a thermoplastic poly (methyl methacrylate)-type polymer is particularly preferred. The second support shell 14 and the lens support tube 25 are preferably made of a material which is highly absorptive of ultrasound, such as polytetrafluoroethylene. The particular material which is used for the first support shell 12 depends on the damping and vibration decay properties desired, and on the mode in which it is desired to have the transducer 22 vibrate. Preferred materials include brass and unpoled PVDF. The first support shell is preferably made of a material which is absorptive of the emitted and reflected wave energies. It is to be understood that the materials preferred for use in the first embodiment are also preferred for use in the other embodiments disclosed hereinbelow.

During operation, the test apparatus 10 and the length of tubing 1 are immersed in water to allow ultrasonic wave energy to be conducted to and from the tubing 1. The tubing 1 is fed axially and nonrotatively though the test apparatus, while the first support shell 12 is maintained in a fixed position and the second support shell 14 is rotated by the toothed belt 18 at a speed on the order of several thousand revolutions per minute.

Periodically, electrical input signals are sent through the transducer 22 by the aforementioned electrical connections, and these electrical input signals cause the transducer 22 to periodically emit bursts of ultrasonic wave energy. As the lens 24 rotates, it focuses the bursts of ultrasound from the transducer 22 onto the tubing 1, and focuses the ultrasound which is reflected from the tubing 1 back onto the transducer 22. When the reflected ultrasonic wave energy hits the transducer 22, it causes the transducer 22 to produce electrical currents therein which are carried from the transducer 22 as electrical output signals by the aforementioned electrical connections.

Thus, as the tubing 1 moves axially through the test apparatus 10, the bursts of ultrasound emitted by the transducer 22 and focused by the lens 24 trace a helical path along the tubing 1. A particular burst of ultrasound will be focused on the tubing 1 by the lens 24, and , after the lens has rotated slightly with the second support shell 14, reflected ultrasonic wave energies reflected from the outside surface of the tubing 1, the inside surface of the tubing 1, and any flaws therebetween will be focused by the lens 24 back onto the transducer 22. The various reflected wave energies then cause the transducer 22 to produce resultant electrical output signals, and these signals can be used to measure the dimensions of the tubing 1 and to detect the presence of flaws in the tubing 1, as will be described hereinbelow with reference to the second, third, and fourth embodiments of the present invention.

Figure 2:
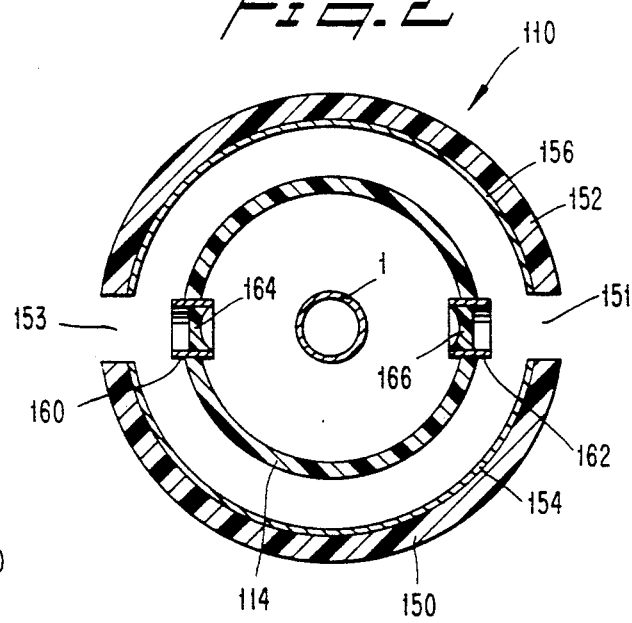
FIG. 2 is a cross-sectional view of a second embodiment of the test apparatus of the present invention.

With reference to FIG. 2, a test apparatus 110 according to a second embodiment of the present invention is designed especially for performing a complete dimensional test on a test object such as a length of tubing 1. The test apparatus 110 is similar to the test apparatus 10, but the test apparatus 110 includes a pair of first semicylindrical support shells 150,152 which are separated by gaps 151, 153, and which each have semicylindrical sheet-like transducers 154, 156 mounted thereon in fixed positions, respectively. Additionally, the test apparatus 110 includes a second rotatable support shell 114 which has a pair of cylindrical lens support tubes 160,162 mounted therein, and a pair of lenses 164,166 mounted inside the support tubes 160,162, respectively. As with the first embodiment, the second support shell 114 may be rotated by a toothed belt, and the lenses 164,166 may be mounted in fixed positions, but they are preferably mounted such that they are movable in a radial direction of the second support shell 114 so that their focal points may be moved to points just at the outer surface of the tubing 1.

The test apparatus 110 operates very similarly to the test apparatus 10. With the test apparatus 110, however, two bursts of ultrasound are fired at the tubing 1 at the same time, and two sets of reflected ultrasound are produced, since the test apparatus 110 includes two separate transducers 154,156 and two rotating lenses 164,166. Therefore, the test apparatus 110 of the second embodiment of the present invention repeatedly produces two sets of electrical output signals which are produced by reflections of ultrasonic wave energy from both the outer and inner surfaces of the tubing 1. Since the time delay between the initial production of ultrasound by the transducers 154,156, and the return of reflected ultrasound to the transducers 154,156 is directly related to the distance the ultrasound has travelled, the electrical output signals from the test apparatus 110 indicate the distance between the transducer 154 and the outer surface of the tubing 1, the distance between the transducer 154 and the inner surface of the tubing 1, the distance between the transducer 156 and the outer surface of the tubing 1, and the distance between the transducer 156 and the inner surface of the tubing 1. Accordingly, since the total distance between the transducers 154,156 is known, the outer diameter, the inner diameter, and the wall thickness of the tubing 1 along each diameter tested by the test apparatus 110 are obtainable from the electrical output signals. The test apparatus 110 according to the second embodiment of the present invention thus provides a relatively simple method for performing a complete dimensional test on a length of tubing.

Figure 3:
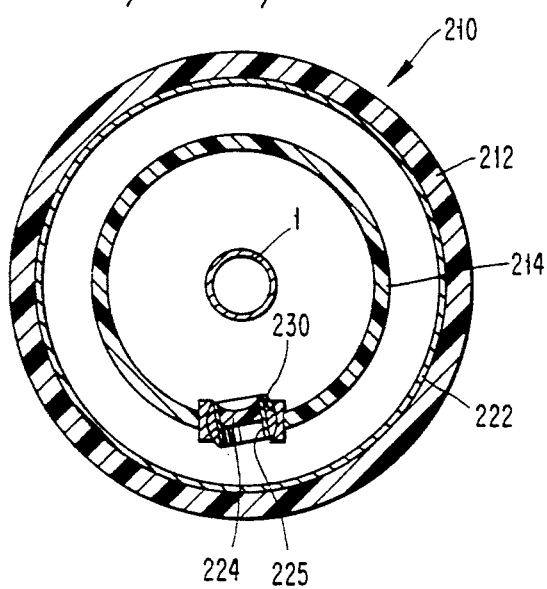
FIG. 3 is a cross-sectional view of a third embodiment of the test apparatus of the present invention.

With reference to FIG. 3, a test apparatus 210 according to a third embodiment of the present invention is constructed very similarly to the test apparatus 10 of the first embodiment, however the test apparatus 210 is design especially to perform a longitudinal flaw test on a test object such as a length of tubing 1.

The test apparatus 210, like the test apparatus 10, includes a first stationary support shell 212, a second rotatable support shell 214 rotatable by a toothed belt (not shown), a sheet-like transducer 222 mounted inside the first support shell 212 in a fixed position, a lens support tube 225 mounted in the wall of the second support shell 214, and a lens 224 mounted in the lens support tube 225, either in a fixed manner or preferably in a radially movable manner. The test apparatus 210 differs from the test apparatus 10, however, in that the lens support shell 225 is mounted in an angularly adjustable mounting 230 such that the lens support tube 225 and consequently the lens 224 are rotatable relative to the second support shell 214 about an axis which is parallel to the longitudinal axis of the second support shell 214.

Accordingly, prior to the start of a test and before rotation of the second support shell 214 is begun, the position and angle of the lens 224 are adjusted within the lens support tube 225 and the mounting 230 such that the lens 224 focuses ultrasonic wave energy from the transducer 222 generally tangentially to the tubing 1. As the tubing 1 is tested, then, ultrasound focused on the tubing 1 travels within the tubing 1 around its circumference. If the ultrasound travelling within the tubing 1 encounters a flaw within the tubing 1, a portion of the ultrasonic wave energy is reflected back from the flaw and is focused on the transducer 222 by the lens 224 to produce an electrical output signal. Thus, due to path which the ultrasound travels within the tubing 1, the test apparatus 210 is especially sensitive to axial defects in the tubing 1, and it therefore provides a relatively simple method of detecting axial defects in lengths of tubing.

With reference to FIG. 4, a test apparatus 310 according to a fourth embodiment of the present invention is constructed and functions very similarly to the test apparatus 210 of FIG. 3. Like the test apparatus 210, the test apparatus 310 includes a first stationary support shell 312, a second rotatable support shell 314 rotatable by a toothed belt (not shown), a cylindrical sheet-like transducer 322 mounted inside the first support shell 312 in a fixed position, an angularly adjustable mounting 330 mounted in the wall of the second support shell 314, a lens support tube 325 mounted in the mounting 330, and a lens 324 mounted in the lens support shell 325, either in a fixed manner or in a radially movable manner.

The difference between the test apparatus 310 and the test apparatus 210 is that the mounting 330 of the test apparatus 310 allows the lens support tube 325 and the lens 324 to be rotated with respect to the second support shell 314 about an axis which is perpendicular to the longitudinal axis of the second support shell 314. Thus, prior to testing of a length of tubing 1 and before the second support shell 314 is rotated, the position and angular orientation of the lens 324 within the lens support tube 325 and the mounting 330 are adjusted such that the focal point of the lens 324 is at a point longitudinally above or below the center of the lens 324. Once testing of a length of tubing 1 has begun, ultrasound which is focused on the tubing 1 by the lens 324 will travel within the tubing 1 along its length. If the ultrasound encounters a flaw in the tubing 1, a portion of the ultrasonic wave energy will be reflected back to the lens 324 and will thus produce an electrical output signal in the transducer 322. Accordingly, due to the path which the ultrasound travels in the tubing 1, the test apparatus 310 provides a relatively simple method of detecting circumferential defects in a length of tubing 1.

With reference to FIGS. 5 and 6, a test apparatus 410 in accordance with a fifth embodiment of the present invention will be described hereinbelow. The test apparatus 410 operates much the same as the apparatuses of the other embodiments, but the test apparatus 410 is designed to test a hollow test object such as a length of tubing 1 from the inside of the object.

Accordingly, the test apparatus 410 includes a first rotatively-fixed cylindrical support shell 412, a second rotatable support shell 414, a cylindrical sheet-like transducer 422 mounted in a fixed position on an outer surface 413 of the first support shell 412, an angularly adjustable mounting 430 mounted in the wall of the second support shell 414, a lens support tube 425 mounted in the mounting 430, and a lens 424 mounted in the lens support tube 425, either in a fixed manner or in a manner such that the lens 424 is movable along a radius of the second support shell 414. As seen in FIG. 5, the test apparatus 410 is arranged within the tubing 1, with the second support shell 414 extending around the first support shell 412 and the transducer 422.

A rack and pinion arrangement 440 attached to a rod 442, wherein the rod 442 is rigidly connected to the first support shell 412, serves to lower and raise the test apparatus 410 within the tubing 1. The second support shell 414 is rotatably mounted around the first support shell 412 and is maintained in a generally central location in the tubing 1 by a pair of spacers 444,446 which extend therearound. The second support shell 414 is preferably rotated by a motor (not shown) located in an upper portion of the test apparatus 410, which drives the second support shell 414 though a gear (not shown) and a toothed ring (not shown) located on an inner surface of the second support shell 414.

As is seen in FIGS. 5 and 6, the angularly adjustable mounting 430 allows the lens support tube 425 and the lens 424 to be rotated about an axis which is parallel to the longitudinal axis of the second support shell 414 and about an axis which is perpendicular to the longitudinal axis of the second support shell 414. The test apparatus 410 is therefore able to perform either a longitudinal flaw test or a circumferential flaw test on a length of tubing 1 once the position and angular orientation of the lens 424 are appropriately adjusted. Additionally, the first support shell 412 may have two separate semicylindrical transducers arranged therearound if desired, to allow the test apparatus 410 to perform a complete dimensional test similar to the test performed by the test apparatus of the second embodiment.

It can readily be seen that each of the above-described embodiments of the present invention incorporates the advantages of the present invention. For example, since the tubing is tested by each of the apparatuses without rotating the tubing, it is possible to test tubing at a relatively high speed with relatively minimal slippage of the tubing occurring. Also, since the transducers in each of the apparatuses are held in rotatively fixed positions, rotating-to-stationary electrical connections are not needed to provide input signals to the transducers and to receive output signals from the transducers. Thus, the apparatuses of the present invention are relatively simple and inexpensive to construct, are much less prone to breakdown, and have generally longer lifetimes than other devices. Additionally, since the lens of the apparatuses are radially and/or angularly adjustable, the apparatuses are each usable to test a wide variety of different-sized tubing with only minimal adjustment.

It is to be understood that various modifications may be made to the apparatuses of the present invention, and advantages of the present invention obtained therefrom. For example, the wave energy emitted by the transducer may be of a type other than ultrasound, and the input and output signals may be other than electrical signals, i.e., they may be light or sound signals. Also, means such as a gear drive or a shaft drive may be used to rotate the second support shell in any of the apparatuses and advantages obtained therefrom. Additionally, the lenses of each of the apparatuses may be movable manually or automatically within the lens support tubes and the angularly adjustable mountings.

If desired, the angularly adjustable mounting of the third or fourth embodiments may be constructed similar to the mounting of the fifth embodiment, so that a single apparatus can be set to perform either circumferential or longitudinal flaw tests, and advantages obtained therefrom. Also, the first support shell of the fifth embodiment may be formed instead as a solid support cylinder, and advantages of the present invention thereby obtained.

The principles, preferred embodiments, and modes of operation of the present invention have been described in the foregoing specification. However, the invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such variations and changes which fall within the spirit and scope of the present invention as defined in the claims be embraced thereby.

It is claimed:

1. A test apparatus for testing tubing using wave energy, comprising:
    a rotationally fixed transducer for receiving an input signal and converting said input signal into an emitted wave energy; and
    a rotating lens through which said emitted wave energy passes for focusing said emitted wave energy onto the tubing, reflected wave energy from the tubing passing through the lens and being focused back onto said transducer, and said transducer receiving said reflected wave energy and converting said reflected wave energy into an output signal.

2. A test apparatus as claimed in claim 1, wherein said transducer is mounted on a first support shell, and said lens is mounted on a second support shell.

3. A test apparatus as claimed in claim 2, wherein said first support shell extends around said second support shell, said transducer is mounted on an inner wall of said first support shell, and said lens is mounted in a wall of said second support shell.

4. A test apparatus as claimed in claim 2, wherein said second support extends around said first support shell, said transducer is mounted on an outer wall of said first support shell, and said lens is mounted in a wall of said second support shell.

5. A test apparatus as claimed in claim 4, wherein said test apparatus further includes means for axially moving said first and second support shells along an inside of a length of the tubing.

6. A test apparatus as claimed in claim 2, wherein said first and second support shells are made of a material which is absorptive of said emitted and reflected wave energies, and said lens is made of a material which is transmissive of said emitted and reflected wave energies.

7. A test apparatus as claimed in claim 1, wherein said apparatus includes a pair of transducers and a pair of rotating lenses, said transducers being mounted on inner walls of a pair of first support shells, respectively, and said lenses being mounted in a wall of a second support shell in positions diametrically opposed to each other, said first support shells extending around said second support shell, and said first support shells being separated by gaps therebetween.

8. A test apparatus as claimed in claim 2, wherein said second support shell is cylindrical, and wherein said apparatus further includes means for moving said lens in a radial direction of said cylindrical second support shell.

9. A test apparatus as claimed in claim 2, wherein said second support shell is cylindrical, and wherein said apparatus further includes means for rotating said lens relative to said second support shell about an axis parallel to a longitudinal axis of said second support shell.

10. A test apparatus as claimed in claim 2, wherein said second support shell is cylindrical, and wherein said apparatus further includes means for rotating said lens relative to said second support shell about an axis perpendicular to a longitudinal axis of said second support shell.

11. A test apparatus as claimed in claim 7, wherein said second support shell is cylindrical, and wherein said apparatus further includes means for moving said lenses in a radial direction of said second support shell.

12. A test apparatus as claimed in claim 1, wherein said emitted and reflected wave energies are ultrasound.

13. A test apparatus for testing tubing using wave energy, comprising:
converting means for converting an input signal into an emitted wave energy, and for converting a reflected wave energy reflected by the tubing into an output signal; and
rotating focusing means through which said emitted wave energy passes for focusing said emitted wave energy from said converting means onto the tubing, and through which said reflected wave energy passes for focusing said reflected wave energy from the tubing onto said converting means.

14. A test apparatus as claimed in claim 13, further including
first rotationally fixed support means for supporting said converting means; and
second rotatable support means for supporting said focusing means.

15. A test apparatus as claimed in claim 14, wherein said first support means includes a first rotationally fixed support shell, said converting means includes a transducer mounted on an inner wall of said support shell, said second support means includes a rotatable support shell, and said focusing means includes a lens mounted in a wall of said second support shell, said first support shell extending around said second support shell.

16. A test apparatus as claimed in claim 14, wherein said first support means includes a first rotationally fixed support shell, said converting means includes a transducer mounted on an outer wall of said first support shell, said second support means includes a second rotatable support shell, and said focusing means includes a lens mounted in a wall of said second support shell, said second support shell extending around said first support shell.

17. A test apparatus as claimed in claim 16, wherein said test apparatus further includes means for axially moving said first and second support shells along an inside of a length of the tubing.

18. A test apparatus as claimed in claim 14, wherein said first support means includes a pair of first rotationally fixed support shells separated by gaps therebetween, said converting means includes a pair of transducers, each of which is mounted on an inner wall of one of said pair of first support shells, said second support means includes a second rotatable support shell, and said focusing means includes a pair of lens mounted in a wall of said second support shell in positions diametrically opposed to each other, wherein said first support shells extend around said second support shell.

19. A test apparatus as claimed in claim 13, further including a rotatable support means which supports said focusing means, wherein said rotatable support means includes a cylindrical rotatable support shell and means for moving said focusing means in a radial direction of said cylindrical shell.

20. A test apparatus as claimed in claim 13, further including a rotatable support means which supports said focusing means, wherein said rotatable support means includes a cylindrical rotatable support shell and means for rotating said focusing means relative to said shell about an axis parallel to a longitudinal axis of said cylindrical shell.

21. A test apparatus as claimed in claim 13, further including a rotatable support means which supports said focusing means, wherein said rotatable support means includes a cylindrical rotatable support shell and means for rotating said focusing means relative to said shell about an axis perpendicular to a longitudinal axis of said shell.

22. A test apparatus as claimed in claim 18, wherein said second support shell is cylindrical, and wherein said second support means further includes means for moving said lens in a radial direction of said second support shell.

23. A test apparatus as claimed in claim 13, wherein said emitted and reflected wave energies are ultrasound.

24. An ultrasonic tubing test apparatus for testing tubing using ultrasound, comprising:
a first cylindrical, rotationally fixed support shell;
a second cylindrical, rotatable support shell located inside said first support shell and disposed around the tubing;
a transducer mounted on an inner wall of said first support shell; and
a lens mounted in a wall of said second support shell such that an electrical input signal inputted to said transducer which is converted by said transducer to ultrasonic wave energy is focused onto the tubing by the lens, and such that ultrasonic wave energy reflected by the tubing is focused by said lens onto said transducer whereby it is converted into an electrical output signal.

25. An apparatus for focusing emitted wave energy from an emitter onto a length of tubing and for focusing reflected wave energy from the tubing onto a sensor, comprising:
a rotatable support shell extending around the tubing, said support shell being made of a material which is absorptive of said emitted and reflected wave energies;

a lens mounted in a wall of said support shell, said lens being made of a material which is transmissive of said emitted and reflected wave energies; and means for rotating said support shell about the tubing, said lens for focusing said emitted wave energy onto the tubing and focusing said reflected wave energy onto the sensor as said support shell rotates.

26. An apparatus as claimed in claim 25, wherein said support shell is cylindrical, and wherein said apparatus further includes means for moving said lens in a radial direction of said support shell.

27. An apparatus as claimed in claim 25, wherein said support shell is cylindrical, and wherein said apparatus further includes means for rotating said lens relative to said support shell about an axis parallel to a longitudinal axis of said support shell.

28. An apparatus as claimed in claim 25, wherein said support shell is cylindrical, and wherein said apparatus further includes means for rotating said lens relative to said support shell about an axis perpendicular to a longitudinal axis of said support shell.

* * * * *